(12) United States Patent
Bergner et al.

(10) Patent No.: US 7,709,688 B2
(45) Date of Patent: May 4, 2010

(54) METHOD FOR THE PRODUCTION OF MENTHOL

(75) Inventors: Eike Johannes Bergner, Schriesheim (DE); Klaus Ebel, Lampertheim (DE); Thorsten Johann, Limburgerhof (DE); Oliver Löber, Freimersheim (DE)

(73) Assignee: BASF SE, Ludwigshafen (DE)

( * ) Notice: Subject to any disclaimer, the term of this patent is extended or adjusted under 35 U.S.C. 154(b) by 320 days.

(21) Appl. No.: 11/720,279

(22) PCT Filed: Nov. 24, 2005

(86) PCT No.: PCT/EP2005/012563

§ 371 (c)(1),
(2), (4) Date: May 25, 2007

(87) PCT Pub. No.: WO2006/056435

PCT Pub. Date: Jun. 1, 2006

(65) Prior Publication Data

US 2008/0139852 A1 Jun. 12, 2008

(30) Foreign Application Priority Data

Nov. 26, 2004  (DE) .................. 10 2004 057 277

(51) Int. Cl.
*C07C 29/17* (2006.01)
*C07C 35/12* (2006.01)

(52) U.S. Cl. ..................... 568/830; 568/829
(58) Field of Classification Search .......... 568/830
See application file for complete search history.

(56) References Cited

U.S. PATENT DOCUMENTS

| | | | |
|---|---|---|---|
| 2,117,414 A | 5/1938 | Glass | |
| 3,254,128 A * | 5/1966 | Hagemeyer, Jr. et al. | .... 568/485 |
| 4,720,327 A | 1/1988 | Aquila et al. | |
| 5,300,706 A | 4/1994 | Immel et al. | |
| 5,663,460 A | 9/1997 | Yamamoto et al. | |
| 5,756,864 A | 5/1998 | Darsow et al. | |
| 6,342,644 B1 | 1/2002 | Sayo et al. | |
| 6,376,422 B1 * | 4/2002 | McNabb et al. | ............. 502/307 |
| 6,706,500 B2 | 3/2004 | Gatfield et al. | |
| 6,716,789 B1 | 4/2004 | Heineke et al. | |
| 6,743,956 B1 | 6/2004 | Haake et al. | |
| 6,916,964 B2 | 7/2005 | Göbbel et al. | |
| 7,101,824 B2 | 9/2006 | Gerlach et al. | |

FOREIGN PATENT DOCUMENTS

| | | |
|---|---|---|
| DE | 31 38 423 | 4/1983 |
| DE | 197 57 297 | 6/1999 |
| DE | 101 60 143 | 6/2003 |
| DE | 10 2004 011 543 | 10/2005 |
| EP | 0 563 611 | 4/1997 |
| EP | 0 926 117 | 6/1999 |
| EP | 0 743 295 | 8/1999 |
| EP | 1 053 974 | 11/2000 |
| EP | 1 225 163 | 7/2002 |
| EP | 1 317 959 | 6/2003 |
| EP | 1 318 129 | 11/2003 |
| EP | 1 013 658 | 11/2004 |
| EP | 1 223 223 | 5/2006 |
| JP | 53116348 | 10/1978 |
| WO | WO-2004/013339 | 2/2004 |
| WO | WO-2005/085160 | 9/2005 |

OTHER PUBLICATIONS

Bauer et al., Common Fragrance and Flavor Materials, 24-47 (2001).*
Takaya et al., 109 J. Amer. Chem. Soc., 1596-1597 (1987).*
Akutagawa, 4 Top. Catal., 271-74 (1997).*
Rojas et al., 286 J. Molec. Catal. A, 70-78 (2008).*
K.H. Schulte-Elte et al., "Über eine aussergewöhnliche Stereospezifität bei der Hydroborierung der diastereomeren (1 R)-Isopulegole mit Diboran," *Helvetica Chimica Acta* (1967), pp. 153-165, vol. 50, No. 21.
Y. Nakatani et al., "A Highly Stereoselective Preparation of *l*-Isopulegol," *Synthesis Comm.* (Feb. 1978), pp. 147-148.
K. Tani et al, "Cationic Rhodium(I) Complex-catalysed Asymmetric Isomerisation of Allylamines to Optically Active Enamines," *J. Chem. Soc., Chem. Commun.* (1982), pp. 600-601, vol. 11.
H. Takaya et al., "Enantioselective Hydrogenation of Allylic and Homoallylic Alcohols," *J. Am. Chem. Soc.* (1987), pp. 1596-1597, vol. 109.
L. D'Accolti et al., "Selective Oxidation of Optically Active sec,sec-1,2-Diols by Dioxiranes. A Practical Method for the Synthesis of Homochiral α-Hydroxy Ketones in High Optical Purity," *J. Org. Chem.* (1993), pp. 3600-3601, vol. 58.
H. Takaya et al., "Asymmetric Hydrogenation of Allylic Alcohols Using Binap-Ruthenium Complexes: (S)-(-)-Citronellol (6-Octen-1-ol, 3,7-dimethyl, (S)-)," *Organic Synthesis*, pp. 74-85, vol. 72, (1995).
S. Akutagawa, "Enantioselective isomerization of allylamine to enamine: practical asymmetric synthesis of (—)-menthol by Rh-BINAP catalysts," *Topics in Catalysis* (1997), pp. 271-274, vol. 4.
K. Bauer et al., "Acyclic Terpenes," *Common Fragrance and Flavor Materials. Preparation, Properties and Uses* (2001), pp. 24-47, Fourth, Completely Revised Edition.
G. Ragagnin et al., "Copper-catalysed aerobic oxidation of alcohols using fluorous biphasic catalysis," *Tetrahedron* (2002), pp. 3985-3991, vol. 58.
S.E. Martin et al., "Efficient solvent-free iron(III) catalyzed oxidation of alcohols by hydrogen peroxide," *Tetrahedron Letters* (2003), pp. 549-552, vol. 44.

* cited by examiner

*Primary Examiner*—Brian J Davis
(74) *Attorney, Agent, or Firm*—Connolly Bove Lodge & Hutz LLP

(57) ABSTRACT

Processes comprising: (a) enantioselectively hydrogenating a staffing material comprising a component selected from geraniol, nerol and mixtures thereof to form optically active citronellol; (b) converting the optically active citronellol to optically active citronellal; (c) cyclizing the optically active citronellal to form a mixture comprising optically active isopulegol; and (d) subjecting the mixture to further processing comprising: (i) separating the optically active isopulegol from the mixture and hydrogenating the separated optically active isopulegol to form optically active menthol; or (ii) hydrogenating the optically active isopulegol in the mixture to form optically active menthol and separating the optically active menthol from the mixture.

20 Claims, No Drawings

METHOD FOR THE PRODUCTION OF MENTHOL

CROSS-REFERENCE TO RELATED APPLICATIONS

This application is a national stage application, under 35 U.S.C. §371, of PCT/EP2005/012563, filed Nov. 24, 2005, which claims priority of German Application No. 10 2004 057 277.1, filed Nov. 26, 2004.

BACKGROUND OF THE INVENTION

The present invention relates to a process for the preparation of optically active menthol from geraniol or nerol or mixtures of geraniol and nerol.

Menthol is one of the most important aroma chemicals, the bulk of which is still isolated from natural sources. For totally synthetic routes to menthol, especially the naturally occurring enantiomer L-menthol, on the industrial scale, there is consequently a constant need to optimize the economics of the process. In particular, the synthesis of L-menthol from inexpensive achiral educts is therefore still a challenge.

L-menthol can be synthesized by pursuing two strategies: On the one hand, racemic menthol, obtainable e.g. by the hydrogenation of thymol, can be obtained after esterification by racemate resolution (by crystallization or enzymatic resolution), as described e.g. in EP-A 0 743 295, EP-A 0 563 611 or EP-A 1 223 223. On the other hand, it is also possible to pursue asymmetric synthesis strategies comprising an enantioselective synthesis step.

STATE OF THE ART

In J. Chem. Soc. Chem. Comm. 1982, 11, 600-601, K. Tani et al. describe the asymmetric synthesis of L-menthol from diethylgeranylamine. In this process, diethylgeranylamine is isomerized to the corresponding optically active enamine in the presence of a cationic Rh(I) complex as catalyst.

JP-A 53-116348 discloses the preparation of L-isopulegol, a precursor of menthol, by the selective cyclization of D-citronellal in the presence of zinc bromide as catalyst.

In Topics in Catalysis 4 (1997) 271-274, S. Akutagawa describes the synthesis of L-menthol by the enantioselective isomerization of allylamines to enamines with Rh-BINAP (BINAP=2,2'-bis(diphenylphosphino)-1,1'-binaphthyl) as catalyst.

In J. Am. Chem. Soc. 1987, 109, 1596-1597 and in Organic Syntheses 1995, 72, 74-85, R. Noyori et al. describe the asymmetric hydrogenation of geraniol by means of an Ru-BINAP catalyst.

U.S. Pat. No. 6,342,644 discloses a process for the asymmetric synthesis of L-menthol by the enantioselective hydrogenation of piperitenone as a key step.

BRIEF SUMMARY OF THE INVENTION

The object of the present invention was to provide a process for the asymmetric synthesis of optically active menthol from one or more inexpensive achiral starting materials which in turn are readily obtainable by synthesis, i.e. do not necessarily have to be isolated from natural sources.

The object was achieved according to the invention by the provision of a process for the preparation of optically active menthol from geraniol or nerol or mixtures of geraniol and nerol by a) enantioselectively hydrogenating geraniol or nerol or mixtures of geraniol and nerol to optically active citronellol, b) converting the resulting optically active citronellol to optically active citronellal, c) cyclizing the resulting optically active citronellal to a mixture of substances containing optically active isopulegol, and d) separating the optically active isopulegol from the resulting mixture of substances and hydrogenating it to optically active menthol, or hydrogenating the optically active isopulegol present in the resulting mixture of substances to optically active menthol and separating the resulting optically active menthol from the mixture of substances obtained as the hydrogenation product.

The starting substance(s) used to carry out the process according to the invention is (are) the compounds geraniol of formula (I) and/or nerol of formula (II):

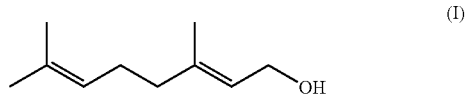

(I)

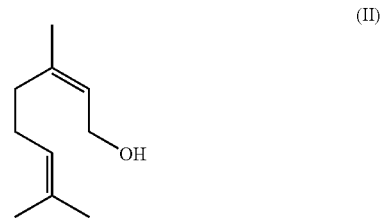

(II)

either individually or in the form of mixtures thereof, it being possible for the individual compounds or the mixtures thereof also to contain small amounts, conventionally of up to about 5% by weight, preferably of up to about 3% by weight, of other compounds or impurities, e.g. solvent residues, water or by-products of previous synthesis steps.

A preferred starting material is geraniol, especially geraniol with a purity of at least 95% by weight, which contains nerol as the major impurity. The geraniol used typically contains about 0.1 to about 5% by weight of nerol. Such mixtures of said compounds are obtained e.g. in the industrial synthesis of geraniol by the selective hydrogenation of citral and subsequent distillative purification, as described e.g. in EP-A 1 317 959, EP-A 1 318 129, DE-A 31 38 423 or DE-A 101 60 143.

In another embodiment of the process according to the invention, it is also possible to use corresponding mixtures of nerol, i.e. nerol containing about 0.1 to about 10% by weight of geraniol, or else pure nerol as starting material.

DETAILED DESCRIPTION OF THE INVENTION

Description of Step a): Enantioselective Hydrogenation

In a first step of the process according to the invention, said starting materials, preferably geraniol, are enantioselectively hydrogenated to optically active citronellol of formula (III):

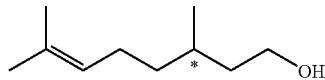

(III)

Optically active citronellol is to be understood here as meaning citronellol that consists predominantly of one of the two possible enantiomers of citronellol. Preferably, within the framework of the present invention, optically active citronellol is to be understood as meaning citronellol having an enantiomeric excess (ee) of at least 90%, preferably of about 95 to about 99%. Here, the asymmetric carbon atom identified by (*) in formula (III) can be in either the R or the S configuration, depending on the chosen reaction conditions and especially on the catalyst used.

The enantioselective hydrogenation is carried out in a manner known to those skilled in the art, in the presence of a suitable catalyst and in the presence of hydrogen. Catalysts that are to be regarded as suitable are those which are capable of enantioselectively hydrogenating trisubstituted ethylenic double bonds, especially those adjacent to a hydroxyl group.

Said enantioselective hydrogenation of step a) is preferably carried out in the presence of a homogeneous transition metal catalyst comprising Ru, Rh or Ir and a chiral ligand containing at least one phosphorus, arsenic and/or antimony atom, preferably at least one phosphorus atom. As mentioned at the outset, such catalysts are known and are described e.g. in T. Ohkuma et al., Asymmetric Synth. (2nd Ed.) 1999, 1-110; Dep. Chem., Res. Cent. Mater. Sci., Nagoya 464, Japan or W. Tang et al., Chem. Rev. 2003, 103, 3029-3069.

Particularly preferred ligands are phosphorus-containing compounds which are capable of forming atropisomers in respect of two aryl or heteroaryl systems, of general formulae (IV) to (VI) below:

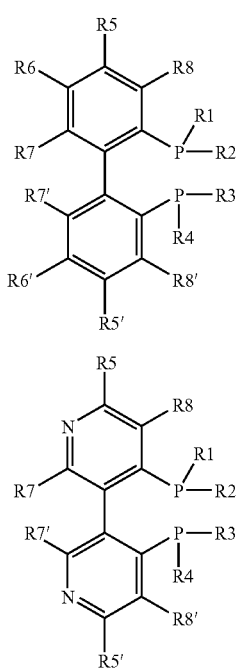

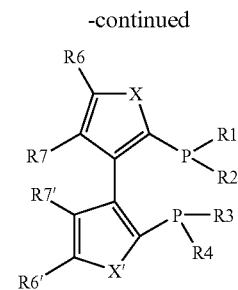

in which the radicals R1 to R10, R5' to R8' and X and X' are defined as follows.

R1, R2 can be identical or different and can be aryl, heteroaryl, alkyl or cycloalkyl having 1 to 20 carbon atoms which is unsubstituted or substituted by halogen, $C_1$- to $C_6$-alkyl or $C_1$- to $C_6$-alkoxy;

R3, R4 can be identical or different and can be aryl, heteroaryl, alkyl or cycloalkyl having 1 to 20 carbon atoms which is unsubstituted or substituted by halogen, $C_1$- to $C_6$-alkyl or $C_1$- to $C_6$-alkoxy;

R5, R5' can be identical or different and can be hydrogen, halogen, $C_1$- to $C_6$-alkyl, $C_6$- to $C_{10}$-aryl, $C_1$- to $C_6$-alkoxy, amino or thio;

R6, R6' can be identical or different and can be hydrogen, halogen, $C_1$- to $C_6$-alkyl, $C_6$- to $C_{10}$-aryl, $C_1$- to $C_6$-alkoxy, amino or thio;

R7, R7' can be identical or different and can be hydrogen, halogen, $C_1$- to $C_6$-alkyl, $C_6$- to $C_{10}$-aryl, $C_1$- to $C_6$-alkoxy, amino or thio;

it being possible for R6 and R7 (if both present) and/or R6' and R7' (if both present) together to form one or more rings which can contain another 1 or 2 double bonds and/or one or more heteroatoms selected from the group comprising N, O and S;

R8, R8' can be identical or different and can be hydrogen, halogen, $C_1$- to $C_6$-alkyl, $C_6$- to $C_{10}$-aryl, $C_1$- to $C_6$-alkoxy, amino or thio; and X, X' can be identical or different and can be S, O or NR9, R9 being hydrogen, $C_1$- to $C_6$-alkyl, $C_6$- to $C_{10}$-aryl, $C_1$- to $C_6$-acyl or $SO_2R10$, R10 being $C_6$- to $C_{10}$-aryl, $C_1$- to $C_6$-alkyl or $C_1$- to $C_6$-fluoroalkyl, especially $CF_3$, and halogen being understood as meaning fluorine, chlorine, bromine or iodine, especially fluorine or chlorine.

$C_1$-$C_6$-alkyl are to be understood as meaning linear, branched or cyclic alkyl radicals having 1 to 6 carbon atoms, e.g. methyl, ethyl, propyl, isopropyl, n-butyl, isobutyl, tert-butyl, n-pentyl, isopentyl, neopentyl, cyclopentyl, n-hexyl or cyclohexyl.

$C_1$- to $C_6$-alkoxy are to be understood as meaning linear or branched alkoxy substituents having 1 to 6 carbon atoms, e.g. methoxy, ethoxy, propoxy or isopropoxy.

$C_6$- to $C_{10}$-aryl are phenyl or naphthyl; heteroaryl is to be understood in particular as meaning pyridyl or thiophenyl.

Amino is —$NH_2$, —NHR11 or —NR11R12, it being possible for R11 and R12 independently of one another to be $C_1$-$C_6$-alkyl.

Thio is to be understood as meaning either free thiol groups —SH or thioethers —SR11.

Particularly suitable ligands for the catalyst systems that are preferably to be used in step a) of the process according to the invention are the following ligands (1) to (43) known from the literature:

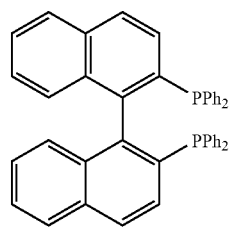 (1)
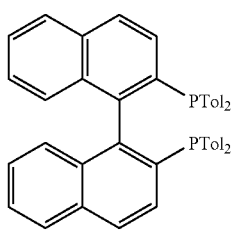 (2)
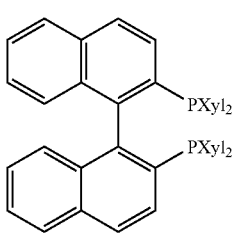 (3)
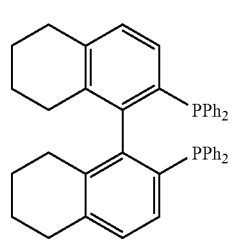 (4)
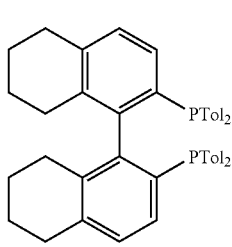 (5)
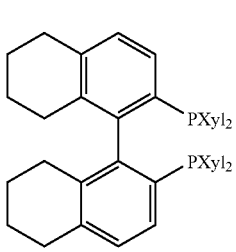 (6)
-continued
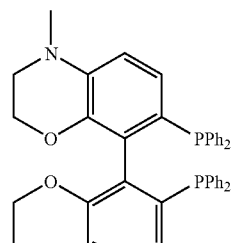 (7)
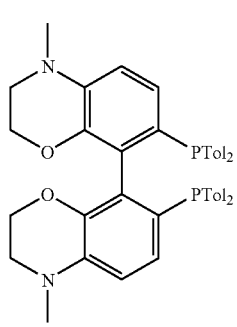 (8)
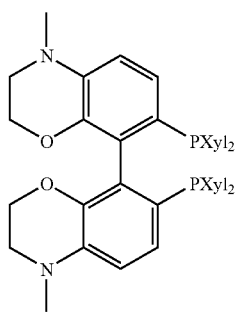 (9)
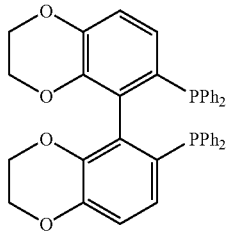 (10)
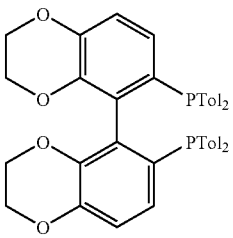 (11)

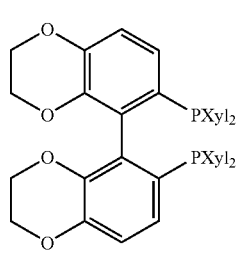
(12)
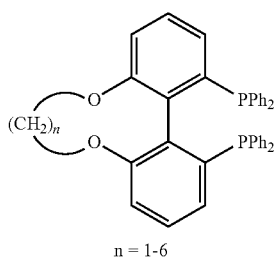
n = 1-6
(13)
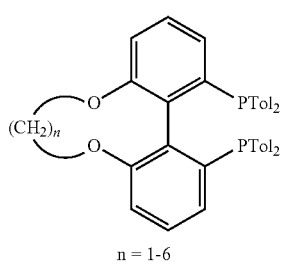
n = 1-6
(14)
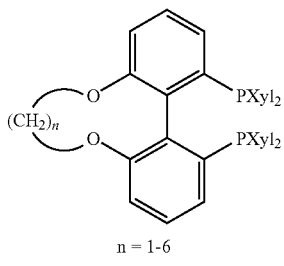
n = 1-6
(15)
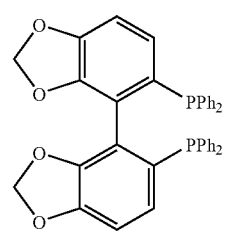
(16)
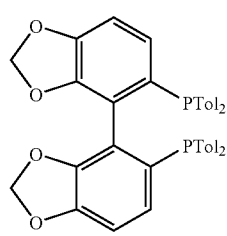
(17)
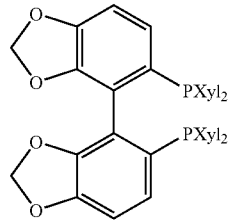
(18)
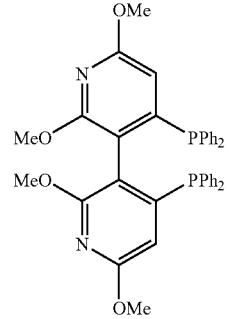
(19)
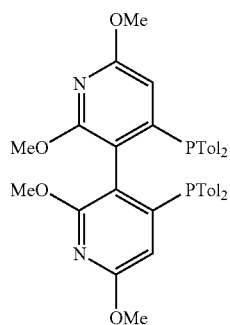
(20)
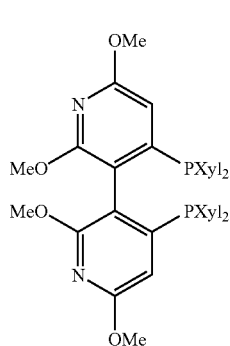
(21)
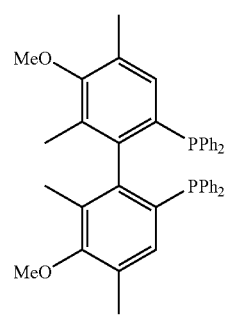
(22)

-continued
(23)
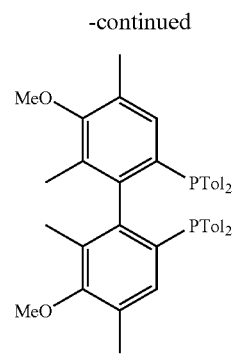
(24)
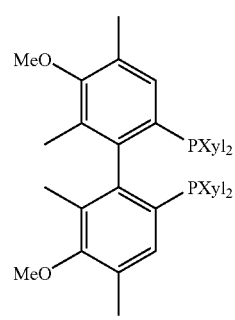
(25)
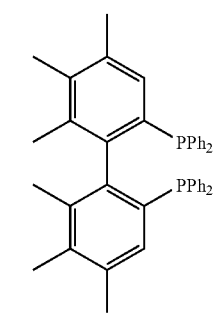
(26)
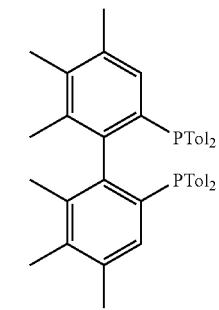
(27)
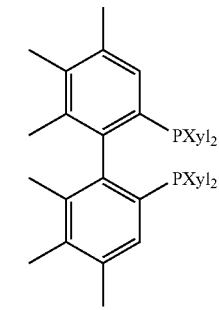
-continued
(28)
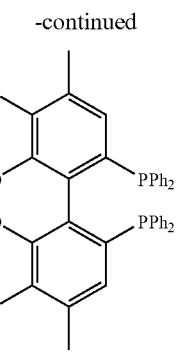
(29)
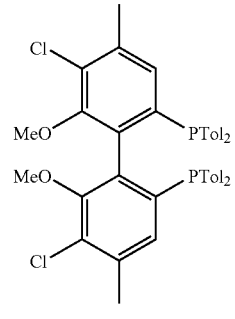
(30)
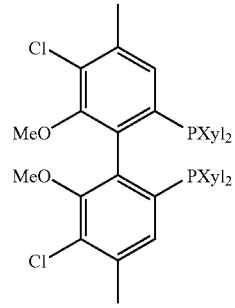
(31)
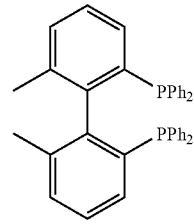
(32)
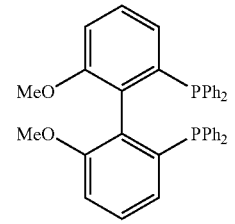
(33)
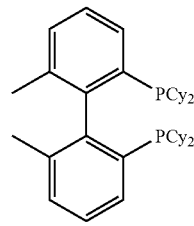

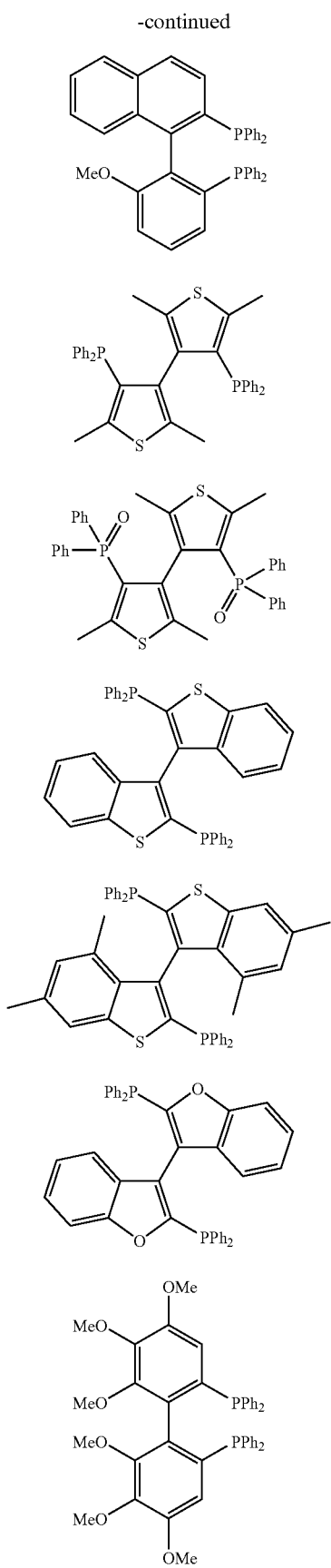

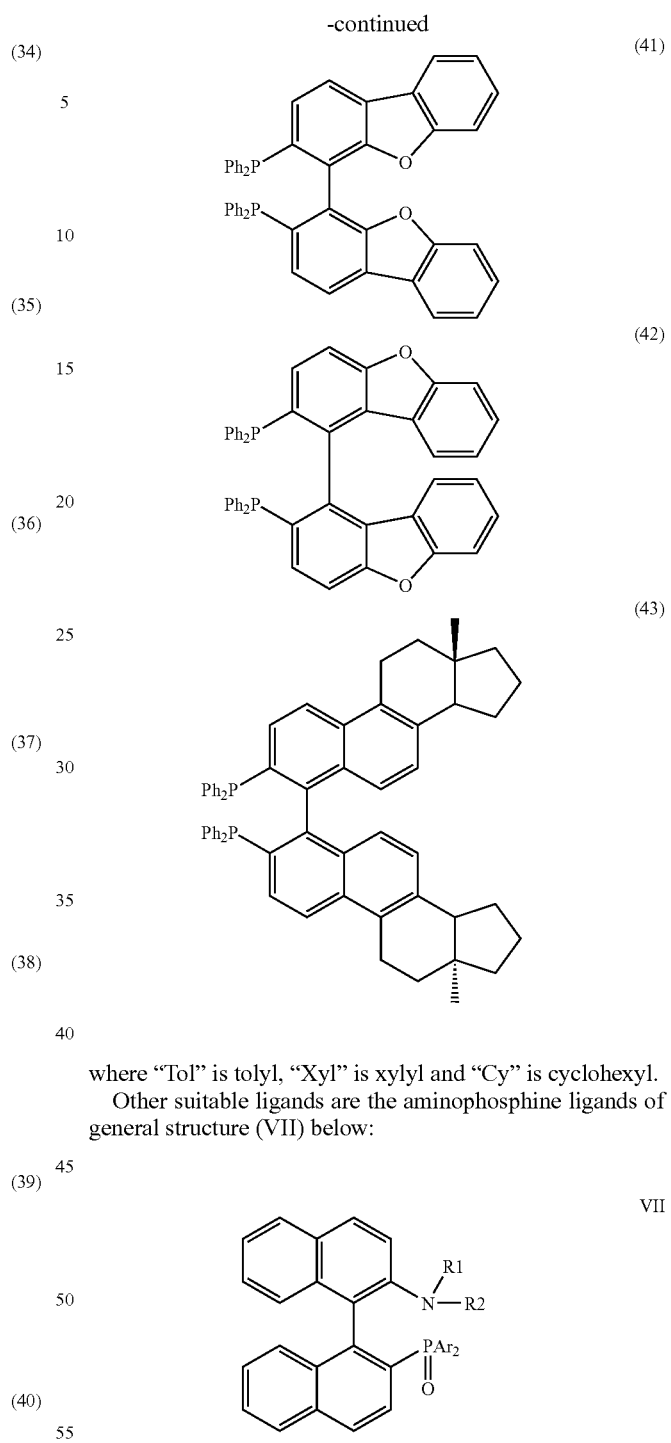

where "Tol" is tolyl, "Xyl" is xylyl and "Cy" is cyclohexyl.

Other suitable ligands are the aminophosphine ligands of general structure (VII) below:

in which

R1, R2 can be as defined above, and

Ar is $C_6$- to $C_{10}$-aryl or -heteroaryl.

Said ligands are preferably used in enantiomerically pure form. Particular preference is given to a catalyst containing Ru and a ligand selected from the group comprising the ligands 2,2'-bis(diphenylphosphino)-1,1'-binaphthyl (BI-NAP), 2,2'-bis[di(p-toyl)-phosphino]-1,1'-binaphthyl (p-Tol-BINAP), 2,2'-bis(diphenylphosphino)-4,4',6,6'-tetramethyl-3,3'-bibenzo[b]thiophene (tetraMetianp) and 2,2'-bis (diphenylphosphino)-3,3'-tetramethyl-3,3'-bibenzo[b]thiophene (bitianp). Very particular preference is given to a catalyst containing Ru and BINAP (2,2'-bis(diphenylphosphino)-1,1'-binaphthyl) (structure (1)) or p-Tol-BINAP (2,2'-bis[di(p-tolyl)phosphino]-1,1'-binaphthyl) (structure (2)), especially (S)-BINAP.

Said transition metal compounds and complexes and other suitable transition metal compounds and complexes are known and are described in the literature or can be prepared by those skilled in the art analogously to the compounds already known.

As is known to those skilled in the art, the two enantiomers of citronellal can specifically be obtained preferentially, depending on the choice of enantiomeric forms of the chiral ligands used and on the configuration of the double bond to be hydrogenated. Thus, for example, D-(R)-citronellol is obtained preferentially by the hydrogenation of geraniol in the presence of a catalyst containing Ru and (S)-BINAP.

If iridium complexes with the aforementioned aminophosphine ligands, e.g. 2-amino-2'-diarylphosphino-1,1'-binaphthyl (SMAP), 2-amino-2'-diarylphosphinyl-1-1'-binaphthyl or 2-carbamoyl-2'-diarylphosphinyl-1-1'-binaphthyl, are used for the asymmetric hydrogenation of geraniol or nerol, it is possible to work with pure nerol or geraniol or even a 1:1 mixture of both terpene alcohols, as described in EP-A 1 013 658.

Said catalysts can be used as finished compounds, some of which are commercially available, or prepared first from precursor compounds in a manner known per se to those skilled in the art. Examples of suitable precursor compounds for the preparation of Ru-containing complexes are [RuCl$_2$(benzene)]$_2$, Ru(acac)$_3$ and [RuCl$_2$(COD)], acac and COD being understood as meaning acetylacetonate and cyclooctadiene respectively.

Conventionally, the chiral ruthenium complexes to be used as catalysts within the framework of the process according to the invention are prepared in situ by bringing the chosen precursor compound into contact with the chosen chiral ligand in a suitable organic solvent and in the absence of oxygen, i.e. preferably under an inert gas atmosphere. It can be advantageous here to add alkali metal or alkaline earth metal salts of acetic acid or trifluoroacetic acid, or acetic acid or trifluoroacetic acid as such, to the mixture.

The molar ratio of ruthenium used (based on the Ru atoms present in the precursor compounds) to chiral ligand used is conventionally about 1:1 to about 2:1, preferably about 1:1.05 to about 1:1.5.

Alkanols, e.g. methanol, ethanol and/or isopropanol, and also alkanediols, e.g. ethylene glycol, diethylene glycol, triethylene glycol and/or tripropylene glycol, have proved particularly suitable solvents for the in situ preparation of the catalyst and for carrying out the enantioselective hydrogenation according to the invention. Furthermore, the hydrogenation can also be carried out successfully without the addition of solvents, i.e. in the pure starting compound.

Particularly preferably, the enantioselective hydrogenation of step a) is carried out using methanol as solvent. The enantioselective hydrogenation of geraniol to citronellol according to the invention is advantageously carried out using a 1 to 50% by weight solution of geraniol in methanol. It is preferable to use a 3 to 20% by weight solution of geraniol in methanol and particularly preferably a 7 to 12% by weight solution.

Said hydrogenation is conventionally carried out in a temperature range from 1 to 60° C., preferably from 20 to 50° C. and particularly preferably from 35 to 45° C., and under a hydrogen pressure of 10 to 150 bar, preferably of 70 to 120 bar. The reaction vessels or reactors to be used do not have to meet any special requirements. Any shapes which ensure a thorough mixing of the reaction mixture, and which those skilled in the art deem appropriate for carrying out reactions under elevated pressure and elevated temperature, are suitable.

By virtue of said measures, the enantioselective hydrogenation of geraniol or nerol to optically active citronellal, according to the invention, can be carried out particularly economically, especially in the case of industrial-scale reactions. Turnover numbers (TON) of up to 10,000 have been achieved, depending on the choice of starting compounds, catalysts and reaction conditions.

The citronellal obtained as described above can be further purified by any of the methods and processes known to those skilled in the art, especially by distillation.

Description of Step b); Conversion to Optically Active Citronellal

In a second step b) of the process according to the invention, the optically active citronellol obtained in step a), as described above, is converted to optically active citronellal of formula (VIII):

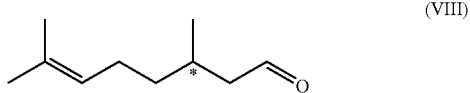

Any processes, methods or reactions (hereafter conversions) which ensure that the enantiomeric excess (ee) of the optically active citronellol achieved in the enantioselective hydrogenation of step a) is substantially preserved are suitable for this purpose. Accordingly, any conversions in which citronellal is obtained with an enantiomeric excess (ee) corresponding to at least 80%, preferably at least 90% and particularly preferably 95 to 100% of the enantiomeric excess of the citronellol obtained in step a) are suitable for carrying out step b) of the process according to the invention.

Examples of suitable reactions for effecting the oxidation or dehydrogenation of optically active citronellal to optically active citronellol, according to the invention, are oxidation with atmospheric oxygen under Fe(NO$_3$)$_3$/FeBr$_3$ catalysis, as described e.g. by S. E. Martin et al. in Tetrahedron Lett. 2003, 44, 549-552, TEMPO oxidation in ionic liquids, as described e.g. by I. A. Ansari et al. in Organic Letters, 2002, 4, 1507-1509, copper-catalyzed aerobic oxidation with TEMPO in a two-phase system containing fluorinated solvents, as described e.g. by G. Ragagnin et al. in Tetrahedron, 2002, 58, 3985-3991, ruthenium-catalyzed aerobic oxidation with TEMPO, e.g. according to A. Dijksman et al., Chem. Commun. 1999, 1591-1591, the selective oxidation of optically active alcohols with dimethyidioxirane, as described e.g. by L. D'Accolti et al. in Org. Chem. 1998, 58, 3600-3601, or the selective oxidation of alcohols with NaOCl and catalytic amounts of TPAP, as described by L. Gonsalvi et al. in Organic Letters, 2002, 4, 1659-1661.

A preferred process for converting optically active citronellol to optically active citronellal in step b), within the framework of the present invention, is the dehydrogenation of optically active citronellol in the presence of a catalyst in the gas phase, as described in the international patent application of file reference PCT/EP/05/002288, which is fully incorporated herein by reference.

A large variety of catalysts, especially those containing at least one element selected from the group comprising zinc, calcium and copper, in each case as such or in the form of suitable compounds, are suitable for carrying out the dehydrogenation process of step b) preferred according to the invention.

Apart from the elements mentioned, the catalysts which can be used according to the invention in step b) can also contain one or more elements from groups 1, 2, 3, 4, 13 and/or 14, e.g. Na, K, Mg, Ti, Zr, C, Si and/or Ge.

Catalysts containing zinc and calcium, preferably in oxidic form and/or in the form of their carbonates, are particularly suitable for carrying out the preferred dehydrogenation process. Catalysts containing zinc oxide and calcium carbonate are particularly preferred.

Preferred catalysts for carrying out the dehydrogenation process are those whose active component contains 30 to 60% by weight, preferably 40 to 50% by weight, of zinc oxide and 40 to 70, preferably 50 to 60% by weight, of calcium carbonates. Other preferred catalysts are those in which the calcium carbonate component is in the calcite modification. Said proportions are to be determined on the calcined catalyst mass containing zinc and calcium in the form of their oxides.

Other catalysts which can be used for the dehydrogenation of optically active citronellol are copper-containing catalysts, especially those containing copper in an oxidation state of >O and in a form deposited on an oxidic support, as described in DE-A 197 57 297. An example of another suitable support is calcium carbonate, inter alia.

In one preferred embodiment, the catalysts which can be used according to the invention have a BET specific surface area of 5 to 50, preferably of 10 to 30 $m^2/g$.

Such a catalyst is obtainable e.g. by precipitating sparingly soluble zinc and calcium compounds from water-soluble zinc and calcium compounds with a base, and then working up in a manner known per se, wherein I. a water-soluble basic carbonate is used as the base,
II. the sparingly soluble zinc and calcium compounds are filtered off, if desired, after precipitation,
III. the zinc and calcium compounds which have been filtered off, if desired, are washed,
IV. the washed zinc and calcium compounds from step III. are dried to give a powder, and then
V. the powder from step IV. is calcined at temperatures not exceeding 600° C., and
VI. the calcined powder is compressed to shaped bodies, if desired.

Water-soluble zinc and calcium salts which can be used are acetates, sulfates, nitrates and chlorides, preferably nitrates, such as zinc nitrate, zinc acetate, zinc sulfate, calcium acetate and calcium nitrate, preferably zinc nitrate and calcium nitrate. It is conventional to use aqueous solutions of the appropriate salts in concentrations ranging from 3 to 25 and preferably from 10 to 25% by weight, and especially of 20% by weight.

The molar ratio of zinc to calcium is preferably chosen so that, after calcination, the active component of the catalyst contains 30 to 60% by weight of zinc oxide and 40 to 70% by weight of calcium carbonate, which is preferably in the calcite modification.

The bases used are water-soluble basic carbonates such as alkali metal carbonates, like sodium carbonate or potassium carbonate, alkali metal hydrogen carbonates, like sodium hydrogen carbonate or potassium hydrogen carbonate, ammonium carbonate or ammonium hydrogen carbonate, and mixtures thereof, preferably sodium carbonate, particularly preferably in the form of aqueous solutions in concentrations ranging generally from 0.5 to 30 and preferably from 10 to 25 grams of base/100 grams of solution.

The precipitation is generally carried out at temperatures ranging from 10 to 90° C., preferably from 40 to 80° C. If desired, the precipitate can be filtered off after precipitation. The precipitate which has been filtered off, if desired, is normally washed with water, preferably until nitrate is no longer detectable by the brown ring test, and then dried, preferably at a temperature ranging from 90 to 150° C., to give a dried powder. The drying can take place in a fixed or moving bed, preferably by spray drying.

The dried powder is then calcined at temperatures not exceeding 600° C., ranging preferably from 300 to 600° C. and particularly preferably from 400 to 475° C., preferably in air. Previous observations have indicated that prolonged heating above 600° C. leads to the formation of the aragonite modification of $CaCO_3$. Brief heating above 600° C. does not hinder the preparation of the catalysts which can be used according to the invention, provided no aragonite is formed (detection by X-ray diffractometry).

After calcination, the calcined powder can be compressed, if desired, to shaped bodies such as tablets, rings, cylinders, etc., preferably tablets.

In one preferred embodiment, the calcined powder is compressed with graphite, preferably 0.1 to 5, particularly preferably 1 to 2.5 and very particularly preferably 2% by weight of graphite, based on the total weight.

In another preferred embodiment, the uncalcined powder from step III. (see above) is compressed to shaped bodies, preferably tablets, annular tablets, domed tablets, as described in U.S. Pat. No. 6,518,220, or trilobes, and the resulting shaped bodies are calcined as described above. An alternative procedure is extrusion to ordinary rods or rods of star-shaped cross-section, preferably ordinary rods.

The calcined powders and shaped bodies obtained in this way can be used as catalysts, it being possible for said catalysts to contain zinc oxide and calcium carbonate (in the calcite modification) as active components and graphite, if desired, as a passive component.

In another preferred embodiment, a dehydrogenation catalyst is used which has a pore volume ranging from 0.10 to 0.50, especially from 0.20 to 0.35 $cm^3/g$, for a pore diameter ranging from 5 nm to 300 mm, particularly preferably at least 85% and very particularly preferably more than 90% of this pore volume being associated with a pore diameter ranging from 0.01 to 0.5 mm.

Particularly preferred catalysts of said type are those which have a transverse compressive strength ranging from 500 to 4000 $N/cm^2$, especially from 1000 to 2500 $N/cm^2$, and a lateral compressive strength of 30 to 300 N, preferably of 50 to 200 N.

The BET specific surface area is generally 5 to 50 $m^2/g$, preferably 10 to 30 $m^2/g$. The pore volume in the pore diameter range between 0.1 nm and 300 nm conventionally has values of between 0.1 and 0.5 $cm^3/g$, preferably of 0.2 to 0.35 $cm^3/g$, with the proviso that at least 85% and preferably more than 90% of this pore volume is in the pore diameter range from 0.01 to 0.5 mm.

The transverse compressive strength of the tablets is preferably 500 to 4000 $N/cm^2$, especially 1000 to 2500 $N/cm^2$, and the lateral compressive strength of the pellets is preferably between 30 and 300 N and particularly preferably 50 to 200 N.

In one particularly preferred embodiment, the precipitate of sparingly soluble zinc and calcium compounds, preferably zinc hydroxide-carbonate and calcium carbonate, is washed on filter presses, the resulting filter cake is slurried with water and the slurry is spray-dried in a spraying tower. The dried spray powder obtained in this way can then be processed further as described above.

Within the framework of the preferred embodiment of step b) of the overall process according to the invention, the vaporized, gaseous, optically active citronellol is brought into contact, in a manner conventional per se, with the dehydrogenation catalyst used, e.g. in a fixed bed reactor, tubular reactor, multitube fixed bed reactor or fluidized bed reactor, preferably in a tubular reactor in which the catalyst is in a fixed arrangement. Multitube fixed bed reactors are particularly preferred. The discharge is conventionally worked up by distillation.

In general, the optically active citronellol used is vaporized in a manner known per se, e.g. in a suitable evaporator.

The dehydrogenation process provided within the framework of the preferred embodiment is conventionally carried out at elevated temperature. The temperature of the gas phase in the reaction zone is conventionally chosen in the range from 350 to 450° C. The pressure of the gas phase in the reaction zone is generally chosen in the range from 0.3 to 10 bar.

The catalyst loading is generally chosen in the range from 0.5 to 3.0 and preferably from 0.6 to 2.0 liters of optically active citronellol per liter of catalyst per hour.

Suitable forms of reactor are the tubular fixed bed reactor and the multitube fixed bed reactor. In these reactors the chosen catalyst is arranged as a fixed bed in a reaction tube or in a bundle of reaction tubes. The reaction tubes are conventionally heated indirectly by burning a gas, e.g. a hydrocarbon such as methane, in the space surrounding the reaction tubes, or by using a heat transfer medium (salt bath, circulating gas, etc.). The reaction tubes can also be heated electrically with heating sleeves. Conventional internal diameters of the reaction tubes are about 2.5 to 15 cm. A typical multitube fixed bed dehydrogenation reactor comprises approx. 10 to 32,000 reaction tubes, preferably approx. 10 to 200 reaction tubes. The temperature inside the reaction tubes conventionally varies in the range from 250 to 600° C., preferably in the range from 300 to 600° C. The operating pressure is conventionally between 0.5 and 8 bar and commonly between 1 and 2 bar.

The preferred dehydrogenation process can also be carried out under heterogeneous catalysis in a fluidized bed, as described in Chem. Eng. Sci. 1992 b, 47 (9-11) 2313. It is advantageous here to operate two fluidized beds next to one another, one of them normally being in a state of regeneration. The operating pressure is typically 1 to 2 bar and the dehydrogenation temperature is normally 250 to 600° C.

The catalytic dehydrogenation preferred according to the invention can be carried out with or without oxygen-containing gas as a co-feed and optionally with the addition of steam, nitrogen, methane and/or argon. The chosen reactor can have one or more catalyst beds in series. The number of catalyst beds can be 1 to 20, advantageously 1 to 6, preferably 1 to 4 and particularly preferably 1 to 3. The reaction gas preferably flows radially or axially through the catalyst beds. In general, such a tray reactor is operated with a fixed bed of catalyst. In the simplest case, the fixed beds of catalyst are arranged in a shaft furnace reactor, either axially or in the annular gaps in concentrically arranged cylindrical grids. A shaft furnace reactor corresponds to a tray.

In one particularly preferred embodiment of the dehydrogenation process of step b) preferred according to the invention, optically active citronellol with an enantiomeric excess of at least 90% ee, preferably of 95% ee, is reacted on a catalyst whose active component contains 54 to 57% by weight of zinc oxide and 43 to 46% by weight of calcium carbonate (determined in each case in the form of the oxides of the calcined catalyst mass), in a suitable reactor, e.g. a tubular reactor. The reactor can be heated by any suitable method, preferably by means of a salt melt, to temperatures ranging from about 350 to about 450° C. The reaction takes place in the gas phase. Good results are obtained particularly when the reaction is carried out in the absence of oxygen. This is done by passing a mixture of substances containing the educt to be hydrogenated, e.g. in a stream of an inert gas such as nitrogen, over the chosen catalyst. Optionally, another possibility is an autothermic procedure involving the partial combustion of $H_2$ after a mixture of substances containing $H_2$ has been fed in.

The reaction products can be isolated by any suitable methods known per se to those skilled in the art. This gives optically active citronellal in a selectivity normally of about 60 to about 95%, with a conversion preferably of about 30 to about 60% of theory.

Description of Step c): Cyclization

The optically active citronellal obtained in step b) of the process according to the invention is cyclized according to the invention to a mixture of substances containing an optically active isopulegol of formula (IX);

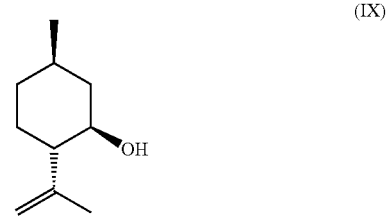

or its enantiomer ent-(IX), depending on the enantiomer of citronellal used. In the cyclization of citronellal to isopulegol, mixtures of the four possible diastereoisomers of isopulegol (isopulegol, neo-isopulegol, iso-isopulegol and neo-iso-isopulegol) are normally obtained, depending on the chosen reaction conditions and the chosen cyclization catalysts. When using optically active citronellal, mixtures of the four diastereoisomers in optically active form are obtained.

The cyclization of step c) of the process according to the invention is conventionally carried out in the presence of an acid or Lewis acid as cyclization catalyst, as described e.g. by Y. Nakatani and K. Kawashima, using zinc halides, in Synthesis, 1978, 147-148 and the references cited therein. Thermal cyclization is also possible, albeit with moderate stereoselectivities (K. H. Schulte-Elte et al., Helv. Chim. Acta 1976, 50, 153-165).

Examples of cyclization catalysts which can be used are $ZnBr_2$, as disclosed e.g. in JP-A 53116348, scandium triflate, as described in EP-A 0 926 117, $SiO_2$ (silica gel), as described in U.S. Pat. No. 2,117,414, mixed oxide catalysts, e.g. $SiO_2$—$Al_2O_3$, montmorillonite, aluminosilicates, iron(III) chloride, zinc chloride, tin tetrachloride and trisdiaryl-phenoxyaluminum complexes, as disclosed in EP-A 1 225 163, or zeolites.

The cyclization of optically active citronellal to mixtures containing optically active isopulegol can be carried out under a wide range of reaction conditions. In particular, the choice of a suitable solvent, the concentration of the substrate in the reaction mixture, and the reaction time and temperature can be varied within wide limits. Furthermore, other forms of energy apart from thermal energy can also be introduced, especially microwave energy or ultrasound. Those skilled in the art preferably choose the reaction conditions so that the cyclization of optically active citronellal in step c) of the process according to the invention (after removal of the solvents) gives a mixture of substances containing at least 60% by weight and preferably at least 75% by weight of isopulegol.

Apart from the desired optically active isopulegol, the mixtures of substances obtained in step c) normally also contain the other three abovementioned diastereoisomers of isopulegol in variable proportions, as well as small amounts of other impurities or solvent residues.

Description of Step d): Separation and Hydrogenation

The resulting mixtures of substances are separated and hydrogenated in step d) of the process according to the invention: either optically active isopulegol is separated from the resulting mixture of substances and hydrogenated to optically active menthol, or the optically active isopulegol present in the resulting mixture of substances is hydrogenated to optically active menthol and the latter is separated from the mixture of substances obtained as the hydrogenation product.

According to the invention, within the framework of a first alternative, the mixtures of substances obtained in step c) can be separated, whereby the optically active isopulegol present in the mixture of substances is separated from the remaining components of the mixture, especially from the other three diastereoisomers of isopulegol.

Any of the methods of separating mixtures of substances, especially mixtures of diastereoisomers, which those skilled in the art deem appropriate are suitable for the separation of step d) of the process according to the invention. Suitable processes for separating off the optically active isopulegol include e.g. crystallization processes, if appropriate after derivatization of the isopulegol diastereoisomers obtained, distillation processes and chromatographic processes. Distillation and crystallization are preferred processes, within the framework of the present invention, for separating off the optically active isopulegol obtained according to the invention. It is possible to increase the optical purity of the isopulegol obtained according to the invention to >99.7% ee, for example by crystallization at low temperatures, e.g. at −40° C., as described in U.S. Pat. No. 5,663,460.

The optically active isopulegol separated off according to this first alternative of step d) of the process according to the invention is then hydrogenated to optically active menthol.

According to the second alternative of step d) of the process according to the invention, the mixtures of substances obtained in step c) can also be hydrogenated first, whereby the optically active isopulegol present in the mixture of substances is hydrogenated to optically active menthol and the latter is separated from the product mixture obtained by hydrogenation.

The separation processes mentioned above for separating off optically active isopulegol are suitable for separating the resulting optically active menthol from any other diastereoisomers and/or impurity that may accompany it.

Any of the hydrogenation processes which those skilled in the art deem appropriate are suitable for the hydrogenation of the ethylenic double bond of the optically active isopulegol or its diastereoisomers, to be carried out in both alternatives, especially processes for the catalytic hydrogenation of ethylenic double bonds on suitable transition metal-containing catalysts in the presence of hydrogen or hydrogen donors. Homogeneous and heterogeneous catalytic processes are equally suitable, heterogeneous catalytic methods being preferable for reactions on the industrial scale. Particularly suitable catalysts are those containing at least one transition metal from groups 7 to 9 of the Periodic Table of the Elements, especially Pd, Pt, Ni, Ir, Rh and/or Ru. Suitable heterogeneous catalysts can be used in either supported or unsupported form. Possible embodiments, process variants or catalysts are within the knowledge of those skilled in the art.

The hydrogenation of isopulegol with Pd suspension catalysts is described e.g. in EP-A 1 053 974. The hydrogenation of different cyclic monoterpene derivatives to menthol is also disclosed in WO 2004/013339.

Step d) of the process according to the invention is preferably carried out by first hydrogenating the mixture of substances obtained in step c) and then separating optically active menthol from the mixture of substances obtained by hydrogenation. Particularly preferably, the optically active menthol obtained by hydrogenation is separated by crystallization from the other components of the mixture of substances obtained by hydrogenation.

In one particularly preferred embodiment of the process according to the invention, geraniol of formula (I), preferably geraniol containing about 0.1 to about 5% by weight of nerol, is enantioselectively hydrogenated to D-(R)-citronellol of formula (X) in step a) of the process according to the invention. A catalyst containing Ru and (S)-BINAP is preferably used here and D-(R)-citronellol with a purity of 90 to 99% ee is preferentially obtained. Within the framework of the particularly preferred embodiment, the resulting D-(R)-citronellol is then converted to D-(R)-citronellal of formula (XI) by dehydrogenation, particular preference being given to a gas phase dehydrogenation as described above. Within the framework of the preferred embodiment, the resulting D-(R)-citronellal is then cyclized to L-isopulegol of formula (IX) in the presence of $ZnBr_2$ or $Al_2O_3/SiO_2$ as catalyst. The L-isopulegol obtained by cyclization is then hydrogenated to L-menthol of formula (XII) as described above, and this is finally separated off by a suitable process, especially crystallization.

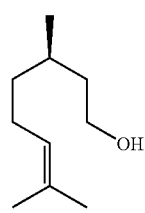

(X)

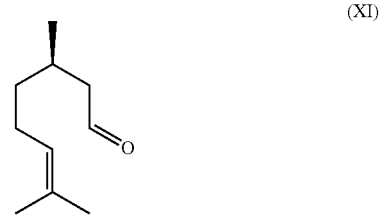

(XI)

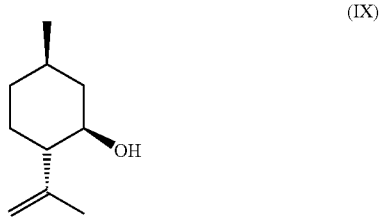

(IX)

-continued

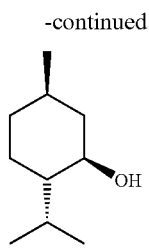

(XII)

The process according to the invention is distinguished by the combination of individual steps a) to d). This combination opens up an advantageous route to optically active menthol which can be carried out satisfactorily on the industrial scale and produces commercially acceptable overall yields. It is of particular importance here that the disclosed synthetic route is independent of starting materials or intermediates that have to be isolated from natural sources, which, if chiral, are normally only available in the form of one of their enantiomers. As a further advantage, the process according to the invention therefore opens up the possibility of alternatively providing both the enantiomers of menthol on the industrial scale.

EXAMPLES

The Examples which follow serve to illustrate the invention without however in any way implying a limitation:

Example 1

Enantioselective Hydrogenation of Geraniol With the Catalyst System Ru/(S)-BINAP Under an inert gas atmosphere, 2.4 mg of [RuCl$_2$(C$_6$H$_6$)]$_2$ (corresponding to 0.01 µmol of Ru) were dissolved in 75 ml of methanol, 6.0 mg (80.01 µmol) of (S)-BINAP were added and the mixture was stirred for 12 h at room temperature until the resulting solution was clear. The catalyst solution was transferred to an autoclave fitted with a gas dispersion stirrer and a further 75 ml of methanol and 14.8 g of geraniol (0.096 mol, purity 95%) were added. The mixture was stirred for 24 h at a hydrogen pressure of 100 bar and a temperature of 40° C. A conversion of 98.3% was then determined by gas chromatography. A yield of 97.2% of (R)-citronellol with an enantiomeric purity of 95.2% ee was obtained.

Example 2

Dehydrogenation of Optically Active Citronellol in the Gas Phase

A tubular reactor heatable by means of a salt melt was charged with 10.8 g of a catalyst consisting of 55% by weight of ZnO and 45% by weight of CaCO$_3$ in the calcite modification (determined in each case in the form of the oxides of the calcined catalyst mass). At a temperature of 400° C., a mixture of 46 Nl/h of nitrogen and 3.44 g/h of (R)-citronellol with an enantiomeric excess of 95% ee was passed over the bed. Citronellal was obtained with an enantiomeric excess of (R)-citronellal of 95% ee, the conversion being 50.2% and the selectivity 75.5%.

What is claimed is:
1. A process comprising:
(a) enauitioselectively hydrogenating a starting material comprising a component selected from geraniol, nerol and mixtures thereof to form optically active citronellol;
(b) converting the optically active citronellol to optically active citronellal;
(c) cyclizing the optically active citronellal to form a mixture comprising optically active isopulegol; and
(d) subjecting the mixture to further processing comprising: (i) separating the optically active isopulegol from the mixture and hydrogenating the separated optically active isopulegol to form optically active menthol; or (ii) hydrogenating the optically active isopulegol in the mixture to form optically active menthol and separating the optically active menthol from the mixture.
2. The process according to claim 1, wherein the starting material comprises geraniol.
3. The process according to claim 1, wherein enantioselectively hydrogenating the starting material is carried out in the presence of a homogeneous transition metal catalyst comprising: a metal selected from the group consisting of Ru, Rh, Ir and combinations thereof; and a chiral ligand comprising at least one phosphorus atom.
4. The process according to claim 1, wherein enantioselectively hydrogenating the starting material is carried out in the presence of a homogeneous transition metal catalyst comprising: a metal selected from the group consisting of Ru, Rh, Ir and combinations thereof; and a ligand which is capable of forming atropisomers in respect of two aryl or heteroaryl systems.
5. The process according to claim 1, wherein enantioselectively hydrogenating the starting material is carried out in the presence of a homogeneous transition metal catalyst comprising Ru and a ligand selected from the group consisting of 2,2'-bis(diphenylphosphino)-1,1'-binaphthyl, 2,2'-bis[di(p-tolyl)phosphino]-1,1'-binaphthyl, 2,2'-bis(diphenylphosphino)-4,4',6,6'-tetramethyl-3,3'-bibenzo[b]thiophene, 2,2'-bis-(diphenylphosphino)-3,3'-tetramethyl-3,3'-bibenzo[b] thiophene and combinations thereof.
6. The process according to claim 1, wherein enantioselectively hydrogenating the starting material is carried out in the presence of a solvent comprising methanol.
7. The process according to claim 1, wherein the starting material comprises a 3 to 20% by weight solution of geraniol in methanol.
8. The process according to claim 5, wherein the starting material comprises a 3 to 20% by weight solution of geraniol in methanol.
9. The process according to claim 1, wherein converting the optically active citronellol to optically active citronellal comprises dehydrogenation in the presence of a catalyst in the gas phase.
10. The process according to claim 9, wherein the catalyst comprises zinc oxide and calcium carbonate.
11. The process according to claim 9, wherein the catalyst comprises 30 to 60% by weight of zinc oxide and 40 to 70% by weight of calcium carbonate, based on a total weight of zinc oxide and calcium carbonate.
12. The process according to claim 1, wherein cyclizing the optically active citronellal to form the mixture is carried out in the presence of an acid or a Lewis acid.
13. The process according to claim 1, wherein cyclizing the optically active citronellal to form the mixture is carried out in the presence of an acid or Lewis acid selected from the group consisting of ZnBr$_2$, scandium triflate, SiO$_2$, SiO$_2$—Al$_2$O$_3$, montmorillonite, aluminosilicates, iron(III) chloride, zinc chloride, tin tetrachloride, trisdiarylphenoxyaluminum complexes, zeolites and combinations thereof.

14. The process according to claim 1, wherein the mixture comprises at least 60% by weight of isopulegol.

15. The process according to claim 1, wherein separating the optically active isopulegol from the mixture comprises distillation, crystallization or both.

16. The process according to claim 1, wherein hydrogenating optically active isopulegol is carried out in the presence of a catalyst.

17. The process according to claim 1, wherein the optically active citronellol comprises D-(R)-citronellol.

18. The process according to claim 1, wherein the optically active citronellal comprises D-(R)-citronellal.

19. The process according to claim 1, wherein the optically active menthol comprises L-menthol.

20. A process comprising:
   (a) enantioselectively hydrogenating a starting material comprising a 3 to 20% by weight solution of geraniol in methanol to form D-(R)-citronellol, wherein enantioselectively hydrogenating the starting material is carried out in the presence of a homogeneous transition metal catalyst comprising Ru and a ligand selected from the group consisting of 2,2'-bis(diphenylphosphino)-1,1'-binaphthyl, 2,2'-bis[di(p-tolyl)phosphino]-1,1'-binaphthyl, 2,2-bis(diphenylphosphino)-4,4',6,6'-tetramethyl-3,3'-bibenzo[b]thiophene, 2,2'-bis-(diphenylphosphino)-3,3'-tetramethyl-3,3'-bibenzo[b]thiophene and combinations thereof;
   (b) converting the D-(R)-citronellol to D-(R)-citronellal;
   (c) cyclizing the D-(R)-citronellal to form a mixture comprising at least 60% by weight of optically active isopulegol; and
   (d) subjecting the mixture to further processing comprising: (i) separating the optically active isopulegol from the mixture and hydrogenating the separated optically active isopulegol to form L-menthol; or (ii) hydrogenating the optically active isopulegol in the mixture to form L-menthol and separating the optically active menthol from the mixture.

* * * * *

UNITED STATES PATENT AND TRADEMARK OFFICE
CERTIFICATE OF CORRECTION

PATENT NO. : 7,709,688 B2  Page 1 of 1
APPLICATION NO. : 11/720279
DATED : May 4, 2010
INVENTOR(S) : Eike Johannes Bergner et al.

It is certified that error appears in the above-identified patent and that said Letters Patent is hereby corrected as shown below:

On the Front Page:

In the Abstract:

"(a) enantioselectively hydrogenating a staffing" should read
--(a) enantioselectively hydrogenating a starting--.

In the Claims:

In claim 1, in column 22, on line 3, "(a) enauitioselectively" should read
--(a) enantioselectively--.

Signed and Sealed this

Fifth Day of October, 2010

David J. Kappos
*Director of the United States Patent and Trademark Office*